United States Patent [19]
Tucker et al.

[11] Patent Number: 5,618,958
[45] Date of Patent: Apr. 8, 1997

[54] CHIRALRHENIUM CATALYSTS AND PROCESSES FOR PREPARING THE SAME

[75] Inventors: Charles E. Tucker; Kenneth G. Davenport, both of Corpus Christi, Tex.

[73] Assignee: Hoechst Celanese Corporation, Somerville, N.J.

[21] Appl. No.: 695,143

[22] Filed: Aug. 8, 1996

[51] Int. Cl.$^6$ .................................................. C07F 13/00
[52] U.S. Cl. .......................... 556/45; 556/46; 556/49; 548/101; 548/106
[58] Field of Search .......................... 556/45, 46, 49; 548/101, 106

[56] References Cited

U.S. PATENT DOCUMENTS 5,155,247   10/1992   Herrmann et al. ...................... 556/46
5,434,116   7/1995    Sone et al. ............................. 556/46 X Primary Examiner—Paul F. Shaver
Attorney, Agent, or Firm—James J. Mullen

[57] ABSTRACT

A novel catalyst comprising the formula:

$$LRE(O)n$$

wherein

L is selected from the group consisting of (a) $(R_1)(AL)$
   wherein $R_1$ is an alkyl side chain containing at least one carbon-rhenium covalent bond, and
   AL is a molecule having $C_2$ to $C_{50}$, and has at least one hetero atom selected from the group consisting of N, O, S, and P wherein there is at least one hetero-rhenium dative bond, and has at least one chiral center. and (b) $R_{AL}$ is a straight or branched chain alkyl or arylalkyl group containing $C_2$ to $C_{50}$ and containing at least one heteroatom selected from the group consisting of N, O, S, and P, with the proviso that said alkyl group contains at least one carbon-rhenium covalent bond and at least one hetero-rhenium dative bond, and has at least one chiral center:
and n is an integer which is 2, 3, 4, or 5 and which has utility in areas such as epoxidation of olefins.

12 Claims, No Drawings

CHIRALRHENIUM CATALYSTS AND PROCESSES FOR PREPARING THE SAME

BACKGROUND OF THE INVENTION

Field of the Invention

The present invention relates to the field of asymmetric catalysis. More particularly, the invention relates to the field of organometallic catalysts useful for enantioselectively epoxidizing prochiral olefins with a new class of organorhenium complexes (i.e., an optically active metal ligand complex catalyst) as novel catalysts.

Asymmetric epoxidation of an olefin constitutes an extremely appealing strategy for the synthesis of optically active organic compounds. Several advances in this area have occurred in recent years. The most commonly and successfully used catalysts for asymmetric epoxidation of unfunctionalized olefins are porphyrin and salen based systems. Chiral metal porphyrins have been reported to catalyze asymmetric epoxidation of styrene derivatives with high turnover numbers and moderate enantioselectivities (J. P. Collman et al. *Science,* 1993, 26, 1404). Unfortunately, the chiral porphyrin systems are usually difficult to prepare and are limited to styrene derivatives as substrates. E. N. Jacobsen (*J. Am. Chem. Soc.* 1990, 112, 2801) and T. Katsuki (Tetrahedron Lett. 1990, 31, 7345) independently reported asymmetric epoxidation of olefins by bleach or iodosobenzene catalyzed by chiral manganese salen complexes. These chiral salen complexes were designed based on Kochi's achiral cationic manganese salen complex that was reported in 1986 (*J. Am. Chem. Soc.* 1986, 108, 2309). The salen based catalyst gave very high enantioselectivities for the epoxidation of cis olefins, e.g., cis-β-methylstyrene and dihydronaphthalene. However, the turnover numbers of these catalysts are typically 10 to 30, and they are limited to conjugated cis olefins. In 1980, Katsuki and Sharpless (references 43 and 44 below) reported a method for the epoxidation of allylic alcohols which proceeds with high enantioselectivities. However, this method is restricted to only allylic alcohols.

While Herrmann et al. (U.S. Pat. No. 5,155,247) have suggested the use of certain organorhenium compounds as catalysts for the oxidation of multiple C-C bonds, these do not produce a chiral epoxide.

Given the broad synthetic utility of chiral epoxides, more efficient catalytic and enantioselective catalysts besides porphyrin, salen and simple rhenium systems for asymmetric epoxidation of unfunctionalized olefins are clearly desirable.

Description of the Prior Art

The following prior art references are disclosed for informational purposes.

1. Herrmann, W. A.; Wagner, W.; Flessner, U. N.; Volkhardt, U.; Komber, H. *Angew. Chem., Int. Ed. Engl.,* 1991, 30, 1636.
2. Herrmann, W. A.; Wang, M. *Angew. Chem, Int. Ed. Engl.,* 1991, 30, 1641.
3. Thiel, W. R.; Fischer, R. W.; Herrmann, W. A. *J. Organomet. Chem.,* 1993, 459, C9.
4. Yamazaki, S.; Espenson, J. H.; Huston, P. *Inorg. Chem.,* 1993. 32, 4683.
5. Huston, P; Espenson, J. H.; Bakac, A. *Inorg. Chem.,* 1993, 32, 4517.
6. Espenson, J. H.; Pestovsky, O.; Huston, P.; Staudt, S. *J. Am. Chem. Soc.,* 1994, 116, 2869.
7. Beattie, I. R.; Jones, J. P.; *Inorg. Chem.,* 1979, 18, 2318.
8. Herrmann, W. A. *J. Organomet. Chem.,* 1986, 300, 111.
9. Herrmann, W. A.; Voss, E.; Floel, M. *J. Organomet. Chem,* 1985, 297, C5.
10. Herrmann, W. A.; Fischer, R. W.; Scherer, W.; Rauch, M. U. *Angew. Chem., Int. Ed. Engl.,* 1993, 32, 1157.
11. Herrmann, W. A.; Fischer, R. W.; Marzz, D. W. *Angew. Chem., Int. Ed. Engl.,* 1991, 30, 1638.
12. Fischer, R. W. Ph.D. Thesis, Technische Universitae Munchen, 1994.
13. Herrmann, W. A.; Romao, C. C.; Fischer, R. W.; Kiprof, P.; de Meric de Beliefon, C. *Angew. Chem., Int. Ed. Engl.,* 1991, 30, 185.
14. Herrmann, W. A.; Kuhn, F. E.; Fischer, R. W.; Thiel, W. R. Romao, C. C. *Inorg. Chem.,* 1992, 31, 4431.
15. Herrmann, W. A.; Ladwig, M.; Kiprof p.; Riede, J. *J. Organomet. Chem.* 1989, 371, C13.
16. Herrmann, W. A.; Kuhn, F. E.; Romao, C. C.; Kleine, M.; Mink, J. *Chem. Ber.,* 1994, 127, 47.
17. Herrmann, W. A.; Kiprof, P.; Rypdal, K.; Tremmel, J.; Blom. R.; Alberto. R.; Behm, J.; Albach, R. W.; Bock, H. Solouki, B.; Mink, J.; Lichtenberger, D.; Gruhn. N. E. *J. Am. Chem. Soc.,* 1991, 113, 6527.
18. Herrmann, W. A. *Angew. Chem., Int. Ed. Engl.,* 1988 27, 1297.
19. Kunkely, H.; Turk, T.; Teixera, C.; de Meric de Bellefon, C. *Organometallics,* 1991, 10, 2090.
20. Mealli, C.; Lopez, J. A.; Calhorda, M. J.; Romao, C. C.; Herrmann, W. A. *Inorg. Chem.,* 1994, 33, 1139.
21. Takacs, J.; Cook, M. R.; Kiprof P.; J. G.; Herrmann, W. A. *Organometallics,* 1991, 10, 316.
22. Takacs, J.; Kiprof P.; Riede, J.; Herrmann, W. A. *Organometallics,* 1990, 9, 782.
23. Herrmann, W. A.; Thiel, W. R.; Herdtweck, E. *Chem. Ber.,* 1990, 123, 271.
24. Herrmann, W. A.; *J. Organometallic Chem.,* 1990, 382, 1.
25. Herrmann, W. A.; Kuchler, J. G.; Weichselbaumer, G.; Herdtweck. E.; Kiprof P. *J. Organometallic Chem.,* 1989, 372, 351.
26. Edwards, P.; Wilkinson, G. *J. Chem. Soc., Dalton Trans.,* 1984, 2695.
27. Schurig, V.; Hintzer, K.; Mark, L. C.; Pitchen, P.; Kagan, H. B. *J. Organomet. Chem.,* 1989, 370, 81.
28. Corey, E. J.; Link, J. O. *Tetrahedron Lett.,* 1992, 33, 4141.
29. Mathre, D. J.; Jones, T. K.; Xavier, L. C.; Blacklock, T. J.; Reamer, R. A.; Mohan. J. J.; Jones, E. T. T.; Hoogsteen, K.; Baum, M. W.; Grabowski, E. J. *J. Org. Chem.,* 1991, 56, 751.
30. Rozema, M. J.; AchyuthaRao, S.; Knochel, P. *J. Org. Chem.,* 1992, 57, 1956.
31. Rozema, M. J.; Eisenberg, C.; Lutjens, H.; Belyk, K.; Knochel, P. *Tetrahedron Lett.,* 1993, 34, 3115.
32. McKillop. A.; Taylor, R. J. K.; Watson, R. J.; Lewis, N. *Synthesis,* 1994, 31.
33. Okada, K.; Samizo, F.; Oda, M. *Chem Lett.,* 1987, 93.
34. Kanai, H.; Matsuda, H. *J. Mol. Cat.,* 1985, 29, 157.
35. Deziel, R.; Goulet. S.; Grenier, L.; Bordeleau, J. *J. Org. Chem.,* 1993, 58, 3619.
36. Sheldon, R. A. "Chirotechnology. Industrial Synthesis of Optically Active Compounds," Marcel Dekker, Inc., 1993, 322.
37. "Chirality in Industry. The Commercial Manufacture and Applications of Optically Active Compounds," Sheldon. R. A., Ed., Wiley, 1992.
38. Sharpless, K. B.; Finn, M. G. in *Asymmetric Synthesis,* Morrison. J. D., Ed., Academic Press, 1985, Vol. 5, 247.
39. Jacobsen, E. N. in *Catalytic Asymmetric Synthesis,* Ojima, I., Ed., VCH Publishers, 1993, 159.

40. Sharpless, K. B.; Johnson, R. A.; in *Comprehensive Organic Synthesis*, Trost, B. M.; Fleming, I., Eds., Pergamon Press, 1991, Vol 7, 389.
41. Kolb, H. C.; Van Nieuwenhze, M. S.; Sharpless, K. B. *Chem. Rev.*, 1994, 94, 2483.
42. Olah, G. A.; Surya Prakash, G. K. *Synthesis*, 1978, 397.
43. Rossiter, B. E.; Katsuki. T.; Sharpless, K. B.; *J. Am. Chem Soc.* 1991, 103, 464.
44. Katsuki, T.; Sharpless, K. B.; *J. Am. Chem. Soc.* 1980, 102, 5974.

SUMMARY OF THE INVENTION

The present invention provides a novel catalyst having the formula:

$$LRe(O)_n$$

wherein L is selected from the group consisting of
(a) $(R_1)$ (AL)
  wherein $R_1$ is an alkyl side chain containing at least one carbon-rhenium covalent bond, and
  AL is a molecule having $C_2$ to $C_{50}$, and has at least one heteroatom selected from the group consisting of N, O, S, and P wherein there is at least one heteroatom-rhenium dative bond, and has at least one chiral center, and
(b) $R_{AL}$ is a straight or branched chain alkyl or arylalkyl group containing $C_2$ to $C_{50}$ and containing at least one heteroatom selected from the group consisting of N, O, S, and P, with the proviso that said alkyl group contains at least one carbon-rhenium covalent bond and at least one heteroatom-rhenium dative bond, and has at least one chiral center:
and n is an integer which is 2, 3, 4, or 5.

Such catalysts have unique utility in areas such as epoxidation of olefins.

DETAILED DESCRIPTION OF THE INVENTION

In one facet of the present invention, there is provided new and novel catalysts having the general formula:

$$LRe(O)_n \qquad (1)$$

wherein
L is selected from the group consisting of
(a) $(R_1)(AL)$
  wherein $R_1$ is an alkyl side chain containing at least one carbon-rhenium covalent bond, and
  AL is a molecule having $C_2$ to $C_{50}$, and has at least one heteroatom selected from the group consisting of N, O, S, and P wherein there is at least one heteroatom-rhenium dative bond, and has at least one chiral center, and
(b) $R_{AL}$ is a straight or branched chain alkyl or arylalkyl group having $C_2$ to $C_{50}$ and has at least one heteroatom selected from the group consisting of N, O, S, and P with the proviso that said alkyl group contains at least one carbon-rhenium covalent bond and at least one heteroatom-rhenium dative bond, and has at least one chiral center;
and n is an integer which is 2, 3, 4 or 5.

Examples of catalysts that fall within formula I include the following:

(a) $(R_1)(AL)ReO_2$ +tm (II)
(b) $R_{AL}ReO_2$ +tm (III)
(c) $(R_1)(AL)ReO_3$ +tm (IV)
(d) $R_{AL}ReO_3$ +tm (V)
(e) $(R_1)(AL)ReO_4$ +tm (VI)
(f) $R_{AL}ReO_5$ +tm (VII)
(g) $(R_1)(AL)ReO_5$ +tm (VIII)
(h) $R_{AL}ReO_5$ +tm (IX)

$R_1$, AL, and $R_{AL}$ have the same definitions as set forth in Formula I.

In the composition as set forth in Formula I, $R_1$ is selected from the group consisting of (a) a non-aromatic hydrocarbon radical having 1 to 10 carbon atoms, and (b) an aralkyl having 6 to 12 carbon atoms, with the proviso that in both (a) and (b) each is bound to rhenium by a carbon atom bearing at least one hydrogen atom.

In other words, $R_1$ is a non-aromatic hydrocarbon radical having 1 to 10 carbon atoms or aralkyl having 6 to 12 carbon atoms, such as benzyl, which in each case is bonded to the rhenium via a carbon atom to which at least one hydrogen atom is still attached, in particular, alkyl radicals having 1 to 10 carbon atoms or cycloalkyl having 5 to 10 carbon atoms. Suitable alkyl radicals are methyl, ethyl, propyl, isopropyl, and the various butyl, pentyl, hexyl or, octyl radicals, such as ethylhexyl and decyl radicals; other suitable radicals are cycloalkyl radicals such as cyclopentyl, cyclohexyl, alkylated cyclohexyl such as hydrogenated tolyl, xylyl, ethyphenyl, cumyl or cymyl, and 1-norbornyl. Particular preference is given to methyl. The terms "alkyl" and "cycloalkyl" naturally imply that the groups contain no multiple bonds.

Examples of AL (from Formula I), which is a chiral molecule, are selected from the group consisting of amine, alcohol, amino alcohol, sulfide, diamine, diol, phosphine, phosphate, sulfite, sulfoxide, imine, and oxazolidine.

In the composition as set forth in Formula I, AL (when selected as a chiral amine) is selected from the group consisting of (a) a primary amine $H_2NR$; (b) a secondary mine $HN(R)_2$; and (c) a tertiary amine $N(R)_3$, with the proviso that in each case, R is independently selected from the group consisting of (1) a branched alkyl having 1 to 18 carbon atoms; (2) an aryl group such as phenyl, naphthyl and anthracyl; and (3) an alkyl group, and there is at least one chiral center.

Examples of the novel catalysts of the present invention include, without limitation, the following formulas which fall within Formula V:

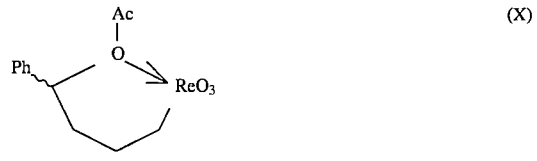
(X)

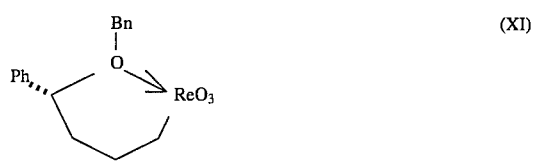
(XI)

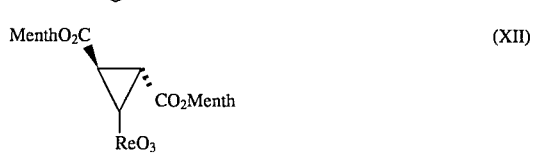
(XII)

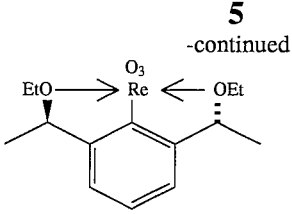

(XIII)

In general, the novel catalysts of the present invention are prepared by the reaction of an organorhenium compound (ORC), such as methytrioxirhenium (MTO), commercially available from Aldrich, with a chiral molecule, such as a chiral amine, in the presence of an organic solvent (e.g. t-butyl alcohol) to form said catalyst. The process is carried out at temperatures of from about −20° C. to about 100° C. and at pressures of subatmospheric, atmospheric or superatmospheric.

This facet of the present invention relates to asymmetric synthesis in which a prochiral or chiral compound is reacted in the process of optically active, metal-ligand complex catalyst, in enantiomerically active form, to produce an optically active product.

Specifically, it has been unexpectedly found that the present invention catalyst can effect asymmetric synthesis in various processes with various substrates to produce material which is optically active.

The asymmetric synthesis processes of this invention are useful for the production of numerous optically active organic compounds, e.g., epoxides, sulfoxides, aziridines, cyclopropanes, aldehydes, alcohols, ethers, esters, amines, amides, carboxylic acids and the like, which have a wide variety of applications.

This part of the subject invention encompasses the carrying out of any known conventional syntheses in an asymmetric fashion with the novel optically active metal-ligand complex catalyst as disclosed herein. As indicated above, the processes of this invention stereoselectively produces one enantiomer from a prochiral starting material, or stereoselectively produces one diasteromer from a chiral starting material. Preferred asymmetric syntheses reactions involve the reaction of organic compounds with an oxygen atom source in the presence of a catalytic amount of an optically active metal-ligand complex catalyst.

More preferably, the subject invention relates to asymmetric epoxidation which involves the use of an optically active metal-ligand complex catalyst in the production of one enantiomer of an epoxide wherein a prochiral or chiral olefinic compound is reacted with an oxygen atom source. The processing techniques of this invention may correspond to any of the known processing techniques heretofore employed in conventional asymmetric synthesis reactions including asymmetric epoxidation reactions.

For instance, the asymmetric synthesis processes can be conducted in continuous, semi-continuous, or batch fashion and involve a liquid recycle and/or gas recycle operation as desired. Likewise, the manner or order of addition of the reaction ingredients, catalyst, and solvent are also not critical and may be accomplished in any conventional fashion.

In general, the asymmetric synthesis reactions are conducted in a liquid reaction medium that contains a solvent for the optically active catalyst, preferably one in which the reaction ingredients, including catalyst, are substantially soluble.

As indicated above, the subject invention encompasses the conducted of any known conventional syntheses in an asymmetric fashion in which the catalyst thereof is replaced by an optically active metal-ligand complex as disclosed herein.

Asymmetric oxidation of sulfides to sulfoxides can be conducted in accordance with conventional procedures known in the art. For example, sulfides can be converted to optically active sulfoxides under oxidation conditions in the presence of an optically active metal-ligand complex catalyst described herein.

Asymmetric oxidation of aldehydes to acids can be conducted in accordance with conventional procedures known in the art. For example, optically active acids can be prepared by reacting a racemic aldehyde and an oxygen atom source in the presence of an optically active metal-ligand complex catalyst described herein.

Asymmetric aziridination can be conducted in accordance with conventional procedures known in the art. For example, prochiral olefins can be converted to optically active aziridines under aziridanation conditions in the presence of an optically active metal-ligand complex catalyst described herein.

Asymmetric aminolysis can be conducted in accordance with conventional procedures known in the art. For example, optically active amines can be prepared by reacting a prochiral olefin with a primary or secondary amine under aminolysis conditions in the presence of an optically active metal-ligand complex catalyst described herein.

Asymmetric isomerization can be conducted in accordance with conventional procedures known in the art. For example, allylic alcohols can be isomerized under isomerization conditions to produce optically active aldehydes in the presence of an optically active metal-ligand complex catalyst described herein.

Asymmetric olefin cyclopropanation can be conducted in accordance with conventional procedures known in the art. For example, optically active cyclopropanes can be prepared by reacting a prochiral olefin and a diazo compound under cyclopropanation conditions in the presence of an optically active metal-ligand complex catalyst described herein.

Asymmetric aldol condensations can be conducted in accordance with conventional procedures known in the art. For example, optically active aldol products can be prepared by reacting a prochiral ketone or aldehyde and an enol ether under aldol condensation conditions in the presence of an optically active metal-ligand complex catalyst described herein.

Asymmetric allylic alkylation can be conducted in accordance with conventional procedures known in the art. For example, optically active hydrocarbons can be prepared by reacting a prochiral ketone or aldehyde and an allylic alkylating agent under alkylation conditions in the presence of an optically active metal-ligand complex catalyst described herein.

Asymmetric Dieis-Alder reaction can be conducted in accordance with conventional procedures known in the art. For example, optically active olefins can be prepared by reacting a prochiral diene and an olefin under cycloaddition conditions in the presence of an optically active metal-ligand complex catalyst described herein.

The permissible prochiral and chiral starting material reactants encompassed by the processes of this invention are, of course, chosen depending on the particular asymmetric synthesis desired. Such starting materials are well known in the art and can be used in conventional amounts in accordance with conventional methods. Illustrative starting material reactants include, for example, substituted and unsubstituted aldehydes (aldol condensation, oxidation to acids, prochiral olefins (epoxidation, aziridination, aminolysis, cyclopropanation, Diels-Alder reaction, ketones (aldol condensation, allylic alkylation), epoxides (nucleophilic ring opening reaction), and alcohols.

The novel catalysts of the present invention thus have utility in a wide variety of chemical processes, and particularly, in asymmetric synthesis reaction which include, without limitation, epoxidation; hydroxylation; cyclopropanation; aziridination; Diels-Alder reactions; cycloaddition; Michael addition; Aldol reaction; allylic alkylation; kinetic resolution; oxidation of aldehydes; olefin isomerization; aminolysis; oxidation of sulfides; oxidation of phosphines; and oxidation of selenides.

While the present invention catalysts have the above illustrated uses, the general discussion herein will focus around the epoxidation of olefins, particularly unfunctionalized olefins.

Illustrative olefin starting material reactants useful in certain of the asymmetric synthesis processes of this invention, e.g., epoxidation, include those which can be terminally or internally unsaturated and be of straight chain, branched chain, or cyclic structure. Such olefins can contain from 3 to 40 carbon atoms or greater and may contain one or more aromatic groups or ethylenic unsaturated groups. Moreover, such olefins may contain groups or substituents which do not essentially adversely interfere with the asymmetric synetheses process such as carbonyl, carbonyloxy, oxy, hydroxy, oxycarbonyl, halogen, alkoxy, aryl, haloalkyl, and the like. Illustrative olefinic unsaturated compounds include substituted and unsubstituted alpha olefins, internal olefins, alkyl alkenoates, alkenyl alkanoates, alkenyl alkyl ethers, alkenols, and the like, e.g. 1-butene, 1-pentene, 1-hexene, 1-octene, 1-decene, 1-dodecene, 1-octa-decene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, aryloates such as vinyl benzoate and the like, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, substituted and unsubstituted chromenes, 3-butenenitrile, 5-hexenamide, styrene, indene, 1,2-dihydronaphthalene, norbornene, alphamethylstyrene, 1,4-naphthoquinone, dimethyl fumarate, methyl cinnamate, and the like. Illustrative preferred olefinic unsaturated compounds include, for example, p-isobutylstyrene, 2-vinyl-6-methoxynaphthylene, 3-ethenylphenyl phenyl ketone, 4-ethylphenyl-2-thienylketone, 4-ethenyl-2-fluorobiphenyl, 4-(1m,3-dihydro-1-oxo-2H-isoindol-2-yl)styrene, 2-ethyl-5-benzoylthiophene, 3-ethenylphenyl phenyl ether, propenylbenzene, isobutyl-4-propenyl-benzene, phenyl vinyl ether, vinyl chloride, and the like. Suitable olefinic unsaturated compounds useful in certain asymmetric syntheses processes of this invention include substituted aryl ethylenes described in U.S. Pat. No. 4,329,507, incorporated herein by reference in its entirety. Of course, it is understood that mixtures of different olefinic starting materials can be employed, if desired, by the asymmetric syntheses processes of the subject invention. More preferably, the subject invention is especially useful for the production of optically active materials, by epoxidation of alpha olefins containing from 3 to 40 carbon atoms or greater, as well as starting material mixtures of such alpha olefins and internal olefins.

Illustrative prochiral and chiral olefins useful in the processes of this invention include those represented by the formula:

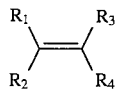

wherein $R_1$, $R_2$, $R_3$, and $R_4$ are the same or different (provided $R_1$ is different from $R_2$ and $R_3$ is different from $R_4$) and are selected from hydrogen; alkyl; substituted alkyl, said substitution being selected from amino including alkyamino and dialkylamino, such as benzylamino and dibenzylamino, hydroxy, alkoxy, such as methoxy and ethoxy, acyloxy, such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzyl- amino; hydroxy, alkoxy such as methoxy and ethoxy, acyloxy such as acetoxy, halo, nitrile, nitro, carboxyl, carboxaldehyde, carboxylic ester, carbonyl, and thio, said aryl substitution being less than four substituents; acyloxy such as acetoxy; alkoxy such as methoxy and ethoxy; amino including alkylamino and dialkylamino such as benzylamino and dibenzyl- amino; acylamino and diacylamino such as acetylbenzylamino and diacetylamino; nitro; carbonyl; nitrile; carboxyl; carboxamide; carboxaldehyde; carboxylic ester; and alkyl- mercapto such as methylmercapto.

It is understood that the prochiral and chiral olefins of this definition also include molecules of the above general formula where the R-groups are connected to form ring compounds, e.g., 2-methyl-1-cyclohexene, and the like.

In accordance with the epoxidation process of the present invention, the prochiral olefin, an oxygen atom source, and the chiral catalyst are reacted under such conditions and for such time as is needed to epoxidize said olefin. In addition to those olefins set forth above, the prochiral olefin can be selected from mono-substituted, 1,1-disubstituted, cis-1,2-disubstituted, trans-1,2-disubstituted, trisubstituted, and tetrasubstituted. Of these, cis-1,2-disubstituted have shown the highest ee values.

Preferably, the prochiral olefin to be epoxidized is selected from the group consisting of cis-disubstituted olefins, including cyclic olefins, bearing a sterically demanding substituent on one end and a smaller substituent on the other end. More preferably, the prochiral olefin is a cis disubstituted olefin with a primary substituent on one side of the double bond and a second, tertiary, or aryl substituent on the other side.

The prochiral olefin can also be selected from the group consisting of enamines, enols, and alpha, beta-unsaturated carbonyls. More preferably, the prochiral olefin is selected from the group consisting of cis-β-methyl-styrene, dihydronaphthalene, 2-cyclohexenyl-1,1-dioxolane, propylene, styrene, and 2,2-dimethylcyclochromene. Most preferably, the prochiral olefin is cis-β-methylstyrene.

The oxygen atom source used in the epoxidation reaction should be an oxidant which is relatively unreactive toward olefins under mild conditions. Preferably, the oxygen atom source is selected from the group consisting of $H_2O_2$, $H_2O_2$ complexes, perboric acid, and oxygen. Thus, a preferred method uses $H_2O_2$ as the oxygen atom source.

The amount of optically active complex catalyst in the reaction medium of a given process of this invention need only be that minimum amount necessary to catalyze the particular asymmetric syntheses process desired. In general, concentrations in the range of from about 1 ppm to about 100,000 ppm, based on the starting reactant, should be sufficient for most asymmetric syntheses processes. For example, in the catalyzed asymmetric epoxidation processes of this invention, it is generally preferred to employ from about 1000 to 50,000 ppm and more preferably from 5000 to 20,000 ppm.

The process conditions employable in the asymmetric processes of this invention are, of course, chosen depending on the particular asymmetric syntheses desired. Such process conditions are well known in the art. All of the asymmetric syntheses processes of this invention can be carried out in accordance with the conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference in their entirety. Depending on the particular process, operating temperatures can range from about −80° C. or less to about 500° C. or greater and operating pressures can range from about 1 psia or less to about 10,000 psia or greater.

The reaction conditions of effecting, for example, the asymmetric epoxidation process of this invention may be those heretofore conventionally used and may comprise a reaction temperature of from about −25° C. or lower to about 200° C. or higher and pressures ranging from about 1 to about 10,000 psia. While one example of the asymmetric syntheses process is the epoxidation of olefinically unsaturated compounds and more preferably olefinic hydrocarbon, to produce optically active epoxides, it is to be understood that the optically active metal-ligand complexes may be employed as catalysts in other types of asymmetric syntheses processes to obtain good results. Moreover, while such other asymmetric syntheses may be performed under their usual conditions, in general, it is believed that they may be performed at lower temperatures than normally preferred due to the optically active metal-ligand complex catalysts.

The total gas pressure of the oxygen atom source and, for example, olefinic unsaturated starting compound of one asymmetric (epoxidation) process of this invention may range from about 1 to about 10,000 psia. More preferably, however, in the asymmetric epoxidation of prochiral olefins to produce optically active epoxides, it is preferred that the process be operated at a total gas pressure of less than about 150 psia, and more preferably less than about 100 psia. The minimum total pressure of the reactants is not particularly critical and is limited predominately only by the amount of reactants necessary to obtain a desired rate of reaction.

In general, the processes of this invention may be conducted at a reaction temperature from about −25° C. or lower to about 200° C. The preferred reaction temperature employed in a given process will, of course, be dependent upon the particular starting material and optically active metal-ligand complex catalyst employed as well as the efficiency desired. Lower reaction temperatures may generally tend to favor higher ee. For example, asymmetric epoxidations at reaction temperatures of about −20° C. to about 120° C. are preferred for all types of olefinic starting materials. More preferably, alpha-olefins can be effectively epoxidized at a temperature of from about 0° C. to about 90° C. while even less reactive olefins than conventional linear alpha-olefins and internal olefins, as well as mixtures of alpha-olefins and internal olefins, are effectively and preferably epoxidized at a temperature of from about 0° C. to about 50° C.

The processes are conducted for a period of time sufficient to produce the optically active products. The exact time employed is dependent, in part, upon factors such as temperature, nature, and proportion of starting materials, and the like. The reaction time will normally be within the range of from about one-half to about 200 hours or more, and preferably from less than about 1 to about 10 hours.

The asymmetric syntheses process (for example, asymmetric epoxidation process) of this invention can be carried out in either the liquid or gaseous state and involve a batch, continuous liquid or gas recycle system, or combination of such systems. A batch system is preferred for conducting the processes of this invention. Preferably, asymmetric epoxidation of this invention involves a batch homogeneous catalysis process wherein the epoxidation is carried out in the presence of any suitable conventional solvent as further outlined herein.

The asymmetric syntheses processes of this invention may be conducted in the presence of an organic solvent for the optically active metal-ligand complex catalyst. Depending on the particular catalyst and reactants employed, suitable organic solvents include, for example, alcohols, alkanes, alkenes, alkenes, ethers, aldehydes, ketones, esters, acids, amides, amines, aromatics, and the like. Any suitable solvent which does not unduly adversely interfere with the intended asymmetric syntheses process can be employed and such solvents may include those heretofore commonly employed in known metal catalyzed processes. Increasing the dielectric constant or polarity of a solvent may generally tend to favor increased reaction rates.

Mixtures of one or more different solvents may be employed if desired. It is obvious that the amount of solvent is not critical to the subject invention and need only be that amount sufficient to provide the reaction medium with the particular metal concentration desired for a given process. In general, the amount of solvent when employed may range from about 5% by weight up to about 95% by weight or more, based on the total weight of the reaction medium.

The processes of this invention are useful for preparing substituted and unsubstituted optically active compounds. The processes of this invention stereo-selectively produce a chiral center. Illustrative optically active compounds prepared by the processes of this invention include, for example, substituted and unsubstituted alcohols or phenols; amines; amides; ethers or epoxides; esters; carboxylic acids or anhydrides; ketones; olefins; acetylenes; halides or sulfonates; aldehydes; nitriles; and hydrocarbons. Illustrative of suitable optically active compounds which can be prepared by the processes of this invention (including derivatives of the optically active compounds described hereinbelow and also prochiral and chiral starting material compounds as described hereinabove) include those permissible compounds which are described in Kirk-Othmer, Encyclopedia of Chemical Technology, Third Edition, 1984, the pertinent portions of which are incorporated herein by reference in their entirety, and The Merck Index, An Encyclopedia of Chemicals, Drugs, and Biologicals, Eleventh Edition, 1989, the pertinent portions of which are incorporated herein by reference in their entirety.

The processes of this invention can provide optically active products having very high enantioselectivity and regioselectivity, e.g., epoxidation. Enantiomeric excesses of preferably greater than 50% can be obtained by the processes of this invention. The processes of this invention can also be carried out at highly desirable reaction rates suitable for commercial use.

The desired optically active products, e.g., epoxides, may be recovered in any conventional manner. Suitable separation techniques include, for example, solvent extraction, crystallization, distillation, vaporization, wiped film evaporation, falling film evaporation, and the like. It may be desired to remove the optically active products from the reaction systems as they are formed through the use of trapping agents as described in WO patent 88/08835.

The optically active products produced by the asymmetric syntheses processes of this invention can undergo further reaction(s) to afford desired derivatives thereof. Such permissible derivatization reactions can be carried out in accordance with conventional procedures known in the art. Illustrative derivatization reactions include, for example, esterification, oxidation of alcohols to aldehydes, N-alkylation of amides, addition of aldehydes to amides, nitrile reduction, acylation of ketones by esters, acylation of amines, and the like.

Illustrative of suitable reactants in effecting the asymmetric synthesis processes of this invention include by way of example:

AL alcohols
PH phenols
THP thiophenols
MER mercaptans
AMN amines
AMD amides
ET ethers
EP epoxides
ES esters
W water
UR ureas
OS oxalates
CN carbamates
CNA carbamic acids
CM carbonates
CMA carbonic acids
CA carboxylic acids
ANH anhydrides
KET ketones
OLE olefins
ACE acetylenes
HAL halides
SUL sulfonates
ALD aldehydes
NIT nitriles
HC hydrocarbons
DZ diazo compounds
BOR boranes
ESE enol silyl ethers
SUD sulfides
PHO phosphines
PHI phosphites
IMI imines Illustrative of suitable optically active products prepared by the asymmetric syntheses processes of this invention include by way of example:

AL alcohols
PH phenols
THP thiophenols
MER mercaptans
AMN amines
AMD amides
ET ethers
EP epoxides
ES esters
UR ureas
OX oxalates
CN carbamates
CNA carbamic acids
CM carbonates
CMA carbonic acids
CA carboxylic acids
ANH anhydrides
KET ketones
OLE olefins
ACE acetylenes
HAL halides
SUL sulfonates
ALD aldehydes
NIT nitriles
HC hydrocarbons
CYP cyclopropanes
ABR alkylboranes
ADL aldols
AZ aziridines
SUO sulfoxides
PPO phosphine oxide
PPA phosphate
OZI oxaziridine Illustrative of asymmetric syntheses reactions encompassed within the scope of this invention include, for example, the following reactant/product combinations:

| REACTANT(S) | PRODUCT(S) |
| --- | --- |
| OLE | EP |
| OLE, HC | HC |
| OLE | AZ |
| SUD | SUO |
| AL | ALD |
| OLE | OLE |
| ALD, ESE | ADL |
| KET, ESE | ADL |
| EP, HCN | NIT |
| ALD | CA |
| PHO | PPO |
| PHI | PPA |
| IMI | OZI |

As indicated above, the processes of this invention can be conducted in a batch or continuous fashion, with recycle of unconsumed starting materials if required. The reaction can be conducted in a single reaction zone or in a plurality of reaction zones, in series, or in parallel, or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and the recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Finally, the optically active products of the process of this invention have a wide range of utility that is well known and documented in the prior art, e.g. they are especially useful as pharmaceuticals, flavors, fragrances, agricultural chemicals, and the like. Illustrative therapeutic applications include, for example, non-steroidal anti-inflammatory drugs, ACE inhibitors, betablockers, analgesics, bronchodilators, spasmolytics, antihistamines, antibiotics, antitumor agents, and the like.

As used herein, the following terms have the indicated meanings:

| | |
|---|---|
| Chiral | molecules which have one or more centers of asymmetry. |
| Achiral | molecules or processes which do not include or involve at least one center of asymmetry. |
| Prochiral | molecules which have the potential to be converted to a chiral product in a particular process. |
| Chiral Center | any structural feature of a molecule that is a site of asymmetry. |
| Racemic | a 50/50 mixture of two (2) enantiomers of a chiral compound. |
| Stereoisomers | compounds which have identical chemical construction, but differ as regards the arrangement of the atoms or groups in space. |
| Enantiomer | stereoisomers which are non-superimposable mirror images of one another. |
| Disstereomer | stereoisomers which are non-superimposable. |
| Stereoselective | a process which produces a particular stereoisomer in favor of others. |
| Enantiomeric Excess (ee) | a measure of the relative amount of two (2) enantiomers present in a product. Enantiomeric excess may be calculated by the formula [amount of major enantiomer − amount of minor enantiomer]/[amount of major enantiomer + amount of minor enantiomer]. |
| Optical Activity | an indirect measurement of the relative amounts of stereoisomers present in a given product. Chiral compounds have the ability to rotate plane polarized light. When one enantiomer is present in excess over the other, the mixture is optically active. |
| Optically Active | a mixture of stereoisomers which rotates plane polarized light due to an excess of one of the stereoisomers over the others. |
| Regioisomers | compounds which have the same molecular formula but differing in the connectivity of the atoms. |
| Regioselective | a process which favors the production of a particular regioisomer. |

For purposes of this invention, the chemical elements are identified in accordance with the Periodic Table of the Elements, CAS version, Handbook of Chemistry and Physics, 67th Ed., 1986–1987, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES (General)

Gas chromatographic (GC) analyses were carried out on Hewlett Packard 5890 instruments equipped with FID detectors. The enantiomeric excesses of the epoxides were determined by chiral GC (Cyclodex B, Chiraldex G-PN) or HPLC (S,S-Whelk-0). $^1$H and $^{13}$C NMR were recorded on Bruker NR200 or Bruker ARX400 spectrometer. Flash Column separations were accomplished using Merck silica gel (230–400 mesh) purchased from Aldrich. Mass spectra were recorded on a Finnigan SSQ 7000 mass spectrometer. The mass of the metal complexes were determined using LCMS with an atmospheric pressure CI interphase.

Unless otherwise indicated, all reactions were carried out under nitrogen. Anhydrous solvents (tBuOMe, tBuOH, THF, MeCn, toluene, $CH_2Cl_2$, ether, and EtOAc) were purchased from Aldrich and used without further purification. Aliquots were taken from the reaction mixtures and analyzed by GC.

Example A

Preparation of Methyltrioxorheniun (MTO)

To a solution of $Re_2O_7$ (5.0 g, 10.3 mmol) in acetonitrile (60 ml) at room temperature in a 3-necked flask equipped with a magnetic stirrer, a nitrogen inlet, a thermometer, and a rubber septum was added trifluoroacetic acid (2.12 g, 10.3 mmol). After stirring for 5 minutes, methytributyltin (6.28 g, 20.6 mmol) was added, and the reaction mixture was stirred at room temperature for 2.5 h. The solvent was then removed under vacuum (0.5 mm Hg) and the remaining solid was then sublimed at 70° C. (0.1 mm Hg) to yield methyltrioxorhenium as colorless crystals (3.96 g, 77%).

Example B

Preparation of Ethyltrioxorhenium (ETO)

To a 3-necked flask equipped with a magnetic stirrer, a gas inlet, a thermometer, and a rubber septum charged, under argon, with a suspension of $Re_2O_7$ (0.489 g, 1.0 mmol) in THF (15 ml) at −78° C. was added $Et_2Zn$ (0.5 mmol) as a solution in hexane (0.5M). The reaction was warmed to −5° C., and the THF was removed under vacuum (1.0 mm Hg). The residue ws then extracted 3×15 ml cold (−50° C.) pentane. The combined pentane extracts were concentrated to approx. 5 ml volume and cooled to −30° C., resulting in the precipitation of ETO as white crystals (0.123 g, 47%).

Examples 1–16

Epoxidation of Olefins with MTO; Chiral Ligands

In each of Examples 1–16, the following procedure was used. To a three-necked flask equipped with a gas inlet, a magnetic stirrer, a thermometer, and a robber septum and charged with $MeReO_3$ (0.20 g, 0.8 mol), chiral ligand (0.28 g, 1.6 mol), and tBuOMe (2.0 ml) and stirred for 30 min at 25° C. and stir for 4 hours. After decomposition of the excess peroxide with $MnO_2$ and ethyl acetate/ammonium chloride work-up, the crude oil was purified by flash column chromatography to yield the product as a clear oil. Chiral column GC showed the enentiomeric excess as indicated. The results are shown in Table 1.

TABLE 1

(MTO)MeReO₃ Catalyzed Epoxidation of Olefins in the Presence of Chiral Ligands

$$\text{Olefin} \xrightarrow[\substack{1.6 \text{ mol \% Chiral Ligand} \\ tBu-O-Me, \ 0°C}]{0.8 \text{ mol \% MTO}} \text{Epoxide}$$

| Yield (%) ee (%) | H₂N-CH(Ph)-CH(Ph)-NH₂ | HO-CH(Ph)-CH-NMe₂ | Me₂N-CH₂-CH(Ph)-OH (Ph) | HO-CH-CH-OH |
|---|---|---|---|---|
| Ph-CH=CH₂ (branched) | (1) 89 / 7 | (2) 90 / 8 | (3) 72 / 3 | (4) 67 / 1 |
| Ph-CH=CH- (trans) | (5) 87 / 8 | (6) 84 / 10 | (7) 80 / 5 | (8) 75 / 3 |
| Ph-CH=CH₂ | (9) 78 / 4 | (10) 68 / 2 | (11) 68 / 0 | (12) 56 / 0 |
| Hex-CH=CH₂ | (13) 91 / 3 | (14) 88 / 4 | (15) 84 / 5 | (16) 67 / 2 |

Examples 17–40

Epoxidation of Olefins with MTO-Chiral Amines

The procedure set forth in Examples 1–16 was utilized in Examples 17–40 with the exception that the mol percent of MTO was 3.0% and the mol percent of the chiral amine was 6.0%. The results of these runs are shown in Table 2.

TABLE 2

$$\text{Olefin} \xrightarrow[\substack{6.0 \text{ mol \% Chiral Ligand} \\ tBu-OH, \ 10°C}]{3.0 \text{ mol \% MTO}} \text{Epoxide}$$

| Yield (%) ee (%) | PhCH(NH₂)Me | PhCH(NMe₂)Me | CyCH(NH₂)Me | bornyl-NH₂ | pinanyl-NH₂ | Naphthyl-CH(NH₂)Me |
|---|---|---|---|---|---|---|
| Ph-CH=CH₂ (branched) | (17) 15 / 76 | (18) 22 / 86 | (19) 60 / 42 | (20) 66 / 33 | (21) 72 / 12 | (22) 73 / 19 |
| Ph-CH=CH- (trans) | (23) 22 / 12 | (24) 82 / 0 | (25) 53 / 6 | (26) 16 / 0 | (27) 45 / 0 | (28) 37 / 15 |
| Ph-CH=CH₂ | (29) NR / — | (30) 87 / 8 | (31) 60 / 0 | (32) 49 / 9 | (33) 32 / 13 | (34) NR / — |
| Hex-CH=CH₂ | (35) 44 / 0 | (36) 51 / 0 | (37) 57 / 0 | (38) 64 / 0 | (39) 70 / 0 | (40) 69 / 0 |

Although the invention has been illustrated by certain of the preceding examples, it is not to be construed as being limited thereby; but rather, the invention encompasses the generic area as herein disclosed. Various modifications and embodiments can be made without departing from the spirit and scope thereof.

What is claimed is:

1. A composition of matter having the formula:

LRe(O)n wherein

L is selected from the group consisting of (a) (R₁)(AL)

wherein $R_1$ is an alkyl side chain containing at least one carbon-rhenium covalent bond, and AL is a molecule having $C_2$ to $C_{50}$, and has at least one heteroatom selected from the group consisting of N, O, S, and P, wherein there is at least one hetero-rhenium atom-dative bond, and has at least one chiral center, and (b) $R_{AL}$ is a straight or branched chain alkyl or arylalkyl group containing $C_2$ to $C_{50}$ and containing at least one heteroatom selected from the group consisting of N, O, S, and P, with the proviso that said alkyl group contains at least one carbon-rhenium covalent bond and at least one hetero-rhenium atom- dative bond and has at least one chiral center; and n is an integer which is 2, 3, 4, or 5.

2. The composition as set forth in claim 1 wherein L is $(R_1)$ (AL) and n is 3, and the formula is $(R_1)(AL)ReO_3$.

3. The composition as set forth in claim 1 wherein L is $R_{AL}$ and n is 3, and the formula is $R_{AL}ReO_3$.

4. The composition as set forth in claim 1 wherein L is $(R_1)(AL)$, and n is 4, and the formula is $(R_1)(AL) ReO_4$.

5. The composition as set forth in claim 1 wherein L is $R_{AL}$ and n is 4, and the formula is $R_{AL}ReO_4$.

6. The composition as set forth in claim 1 wherein L is $(R_1)(AL)$ and n is 5, and the formula is $(R_1)(AL)ReO_5$.

7. The composition as set forth in claim 1 wherein L is $R_{AL}$ and n is 5, and the formula is $R_{AL}ReO_5$.

8. The composition as set forth in claim 1 wherein L is $(R_1)(AL)$ an n is 2, and the formula is $(R_1)(AL)ReO_2$.

9. The composition as set forth in claim 1 wherein L is $R_{AL}$ and n is 2, and the formula is $R_{AL}ReO_2$.

10. The composition as set forth in claim 1 wherein $R_1$ is selected from the group consisting of (a) a non-aromatic hydrocarbon radical having 1 to 10 carbon atoms, and (b) an arylalkyl having 7 to 9 carbon atoms, with the proviso that in both (a) and (b), each is bound to rhenium by a carbon atom having at least one hydrogen atom.

11. The composition as set forth in claim 1 wherein AL is a chiral amine which is selected from the group consisting of (a) a primary amine $H_2NR$, (b) a second amine $HN(R)_2$, and (c) a tertiary amine $N(R)_3$, with the proviso that in each case, R is independently selected from the group consisting of (1) a branched alkyl having 1 to 18 carbon atoms, (2) an aryl group, and (3) an alkaryl group, and there is at least one chiral center.

12. The composition as set forth in claim 1 wherein AL is a chiral molecule selected from the group consisting of amine, alcohol, aminoalcolhol, sulfide, diamine, diol, phosphine, phosphate, sulfite, sulfoxide, imine, ester, amide, oxazoline, and oxazolidine.

* * * * *